(12) United States Patent
Deuerling-Zheng et al.

(10) Patent No.: US 8,488,861 B2
(45) Date of Patent: Jul. 16, 2013

(54) SYSTEM AND METHOD OF AUTOMATIC ESTIMATION OF ARTERIAL INPUT FUNCTION FOR EVALUATION OF BLOOD FLOW

(75) Inventors: Yu Deuerling-Zheng, Erlangen (DE); Jan Boese, Eckental (DE); Michael Zellerhoff, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 1117 days.

(21) Appl. No.: 12/245,373

(22) Filed: Oct. 3, 2008

(65) Prior Publication Data

US 2009/0092308 A1  Apr. 9, 2009

Related U.S. Application Data

(60) Provisional application No. 60/977,745, filed on Oct. 5, 2007.

(51) Int. Cl.
*G06K 9/60* (2006.01)
*G06K 9/78* (2006.01)
*G06K 9/80* (2006.01)
*H05G 1/60* (2006.01)

(52) U.S. Cl.
USPC .......... 382/132; 382/130; 382/133; 382/134; 378/98.11; 378/98.12

(58) Field of Classification Search
USPC  382/128, 130–134, 276, 279, 325; 378/4–20, 378/62, 91, 98, 98.8, 98.11, 98.12, 204, 210, 378/901
See application file for complete search history.

(56) References Cited

U.S. PATENT DOCUMENTS

| 6,983,182 B2* | 1/2006 | Mistretta | 600/425 |
| 7,233,689 B2* | 6/2007 | Haupert et al. | 382/130 |
| 2004/0081271 A1* | 4/2004 | Hayashi | 378/25 |

FOREIGN PATENT DOCUMENTS

WO  WO 2005112753 A2 * 12/2005

OTHER PUBLICATIONS

Burbank, F., et al., "Effect of Volume and Rate of Contrast Medium Injection on Intravenous Digital Subtraction Angiographic Contrast Medium Curves," ©1984 by the American College of Cardiology, JACC vol. 4, No. 2, Aug. 1984, pp. 308-315.

Petrella, J., et al., "MR Perfusion Imaging of the Brain: Techniques and Applications," AJR: 175, 2000; ©American Roentgen Ray Society, pp. 207-219.

Ostergaard, L., "Principles of Cerebral Perfusion Imaging by Bolus Tracking," ©2005 Wiley-Liss, Inc., Journal of Magnetic Resonance Imaging 22, pp. 710-717.

* cited by examiner

*Primary Examiner* — Anastasia Midkiff
(74) *Attorney, Agent, or Firm* — Lempia Summerfield Katz LLC

(57) ABSTRACT

A system and method of determining hemodynamic parameters of a patient is described. A background image data set is obtained prior to the administration of a contrast agent. A series of image data sets is obtained during the first passage of the bolus through a parenchymal volume. The pre-contrast-agent image is subtracted from image data sets obtained during the first passage of the contrast agent bolus, so that the amount of contrast agent in the volume may be determined. The time series of the amount of contrast agent is computed to determine the arterial input function (AIF) which may be used to determine a tissue impulse response, and hemodynamic parameters such as cerebral blood flow (CBF), cerebral blood volume (CBV) and mean transit time (MTT).

20 Claims, 5 Drawing Sheets

SYSTEM AND METHOD OF AUTOMATIC ESTIMATION OF ARTERIAL INPUT FUNCTION FOR EVALUATION OF BLOOD FLOW

This application claims the benefit of priority to U.S. provisional application 60/977,745, filed on Oct. 5, 2007, which is incorporated herein by reference.

TECHNICAL FIELD

The present application relates to the diagnosis and treatment of cerebral syndromes where the evaluation of hemodynamic parameters is useful.

BACKGROUND

Medical imaging, such as X-ray, CT (computed tomography), MR (magnetic resonance imaging), PET (positron emission tomography), and the like have become important clinical tools for evaluation of brain function. One such functional parameter is the cerebral perfusion, which characterizes the passage of blood through the vessels of the brain. Such evaluation procedures are non-invasive or minimally invasive, and may measure the cerebral perfusion by a variety of hemodynamic measurements such as cerebral blood volume (CBV), cerebral blood flow (CBF) and mean transit time (MTT).

The measurement technique may include the administration of contrast agents (which may also be called "tracers"), the tracers being selected as appropriate for the imaging modality. For example, paramagnetic contrast material may be used in MR, and iodinated radiographic contrast material is used for X-ray based modalities.

Using a model of the physiology by which the contrast agent passes through the organ, the hemodynamic parameters may be determined. In the case of the brain, the blood-brain barrier is presumed to restrict the contrast agent to the vascular system and that there is no diffusion in to the extravascular space occupied by the brain tissue. The imaging may be performed as a series of dynamic images during the bolus injection, or after an equilibrium state has been reached.

Dynamic imaging enables visualization and measurement of the first pass of the bolus of contrast agent through the organ to be evaluated. In the case of the brain, the time for a bolus to make a first pass is approximately 20 seconds. A signal representing the concentration of tracer can be evaluated to characterize the hemodynamics.

While the definitions of cerebral blood volume (CBV), cerebral blood flow (CBF), and mean transit time (MTT) may have some variation in the literature, CBV may be considered to refer to the volume of blood in a given region of brain tissue and is measured as milliliters per 100 grams of brain tissue. CBF refers to the volume of blood per unit time passing through a given region of brain tissue, and is measured in milliliters per minute per 100 grams of brain tissue; and, MTT refers to the average time taken for blood to pass through a given region of brain tissue, and is measured in seconds. Other characterizing measurements may also be performed.

In the clinical practice, the tracer or contrast agent is usually injected manually during an angiographic examination. Only in few cases, e.g., for specific clinical studies where the exact protocol of injection is required, will automatic injection with a power injector be utilized. In the routine clinical case, usually only the total dose of the tracer injected during the whole angiographic procedure will be recorded. The doses of the tracer and the injection rate for an individual image data set acquisition may not have been recorded.

A common method of analyzing the images is to measure the tracer intensity profile in the main feeding artery as representative of the input function. In the case of an artery of the brain, this is termed the arterial input function (AIF). This analysis is typically performed by manually selecting a portion of the image representing a region of the feeding artery and extracting the time-concentration-curve of the tracer at this region. This may be aided by narrowing the selection to a small group of pixels chosen using an automated algorithm which searches the entire image data for pixels with time-concentration curves that satisfy criteria characteristics of arteries, such as large peak, early arrival time, and short mean transit time. This may require the manual establishment of time and intensity thresholds.

SUMMARY

A system for determining arterial input function automatically for the purpose of calculating hemodynamic parameters of a patient is described, including a medical imaging device and a computer. The computer is adapted to receive a first image data set from the medical imaging device and to receive a plurality of temporally resolved second image data sets from the medical imaging device, the second image data sets being obtained after administration of a contrast agent. The first image data set is subtracted from each of a series of second image data sets to form a plurality of third image data sets. The pixel or voxel data of the image data sets of the third image data are summed to determine the amount of contrast agent for each of the image data sets of the third image data set; this results in a time series of values of contrast agent amount which is differentiated with respect to time to obtain the AIF.

A method of determining hemodynamic parameters, is described, including: receiving a first image data set of a patient; receiving a plurality of second image data sets of the patient, the second image data sets being obtained during a first passage of a contrast agent bolus through a parenchyma; computing a plurality of third image data sets by subtracting a value of each element of the first data set from a value of a corresponding element in the second image data sets; computing the amount of contrast agent in the parenchyma for image data sets of the third image data sets; computing a time derivative of the amount of contrast agent to determine an arterial input function; and, de-convolving the arterial input function from the tissue time-concentration curve to determine a tissue impulse response.

A computer program product is described, the product stored or distributed on a computer readable memory, including instructions configuring a computer to receive a first image data set of a patient; receive a plurality of temporally resolved second image data sets of the patient, the second image data sets being obtained during a first passage of a contrast agent bolus through a parenchyma; compute a plurality of third image data sets by subtracting a value of intensity of each element of the first data set from a value of intensity of a corresponding element in the second image data sets; compute an amount of contrast agent in the parenchyma for image data sets of the third image data sets; compute a time derivative of the amount of contrast agent to determine an arterial input function (AIF).

DETAILED DESCRIPTION

Figure 1:
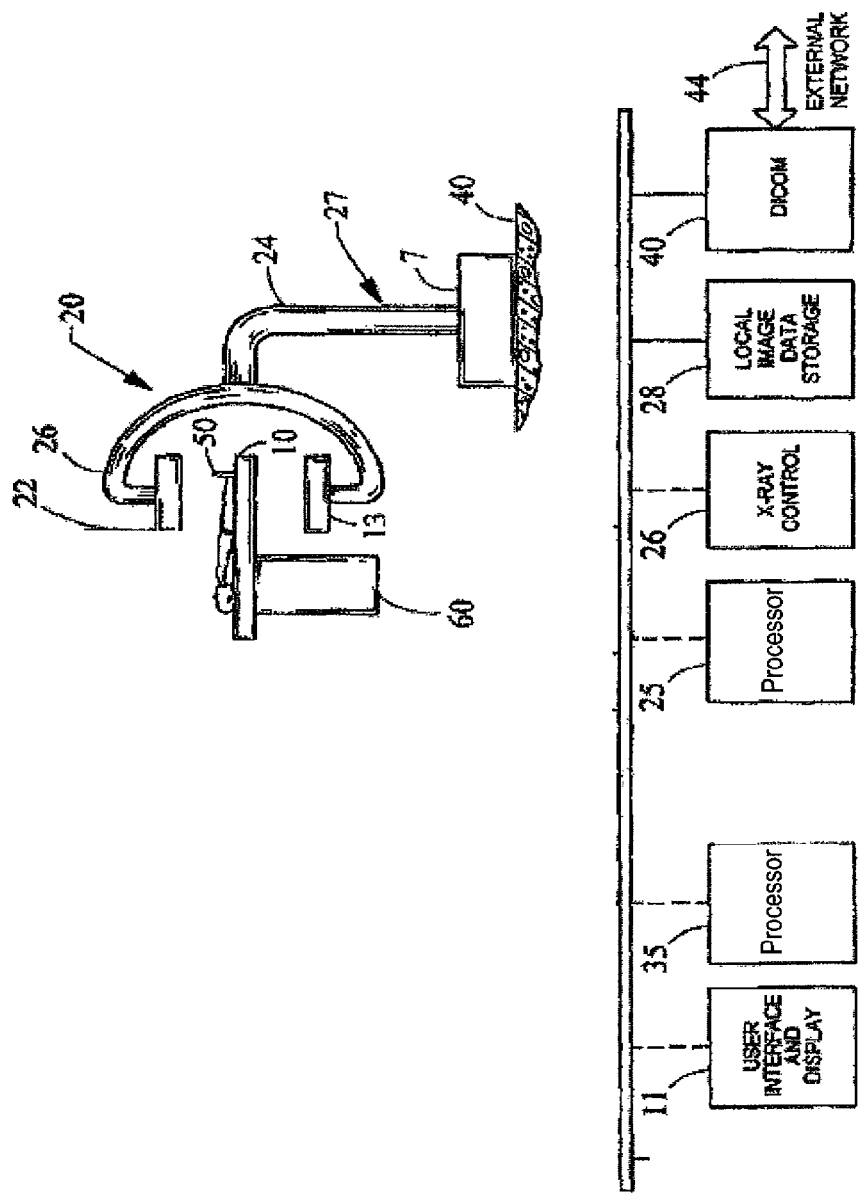
FIG. 1 is a block diagram of a radiological suite having a C-arm X-ray device.

Exemplary embodiments may be better understood with reference to the drawings. Like numbered elements in the same or different drawings perform equivalent functions.

The examples of diseases, syndromes, conditions, and the like, and the types of examination and treatment protocols described herein are by way of example, and are not meant to suggest that the method and apparatus is limited to those named, or the equivalents thereof. As the medical arts are continually advancing, the use of the methods and apparatus described herein may be expected to encompass a broader scope in the diagnosis and treatment of patients.

When describing a medical intervention technique, the terms "non-invasive," "minimally invasive," and "invasive" may be used. Generally, the term non-invasive means the administering of a treatment or medication while not introducing any treatment apparatus into the vascular system or opening a bodily cavity. Included in this definition is the administering of substances such as contrast agents using a needle or port into the vascular system. Minimally invasive means the administering of treatment or medication by introducing a device or apparatus through a small aperture in the skin into the vascular or related bodily structures. Invasive means open surgery.

The combination of hardware and software to accomplish the tasks described herein may be termed a platform. The instructions for implementing processes of the platform may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, microcode and the like, operating alone or in combination. Some aspects of the functions, acts, or tasks may be performed by dedicated hardware, or manually by an operator.

The platform may be a radiological laboratory, and may include ancillary computing and telecommunications devices and networks, or access thereto. Other aspects of the platform may include a remotely located client computer. The client computer may have other functions not related to the platform described herein, and may therefore be shared between users having unrelated functions.

The computer instructions for a processing device may be stored on a removable media device for reading by local or remote systems or processors. In other embodiments, the instructions may be stored in a remote location for transfer through a computer data network, a local area network (LAN) or wide area network (WAN) such as the Internet, by wireless techniques, or over telephone lines. In yet other embodiments, the instructions are stored within a given computer, system, or device.

Where the term "data network", "web" or "Internet" is used, the intent is to describe an internetworking environment, including both local and wide area networks, where defined transmission protocols are used to facilitate communications between diverse, possibly geographically dispersed, entities. An example of such an environment is the world-wide-web (WWW) and the use of the TCP/IP data packet protocol, and the use of Ethernet or other known or later developed hardware and software protocols for some of the data paths.

Communications between the devices, systems and applications may be by the use of either wired or wireless connections. Wireless communication may include, audio, radio, lightwave or other technique not requiring a physical connection between a transmitting device and a compatible receiving device. While the communication may be described as being from a transmitter to a receiver, this does not exclude the reverse path, and a wireless communications device may include both transmitting and receiving functions. A wireless communications connection may include a transceiver implementing a communications protocol such as IEEE 802.11b/g, or the like, such that the transceivers are interoperable.

Where the term "client" is used, a computer executing a program of stored instructions and accepting input from a person, and displaying data, images or the like, in response to such input is meant. Corresponding to the client is another computer, the "server", that retrieves the data, images, or the like in response to requests received from the client, and transmits the data as information over a communications network. It will be understood by persons of skill in the art that often a computer may act as both a client and a server, and that networks may have intermediate computers, storage devices and the like to provide the functional equivalent of a client and a server interaction protocol. There is no implication herein that any of the functions capable of being performed by a digital computing device, including storage and display devices is restricted to being performed on a specific computer, or in a specific location, even though the description may use such locations or designations for clarity in the examples provided.

The arterial input function AIF may be used when determining various tissue hemodynamic parameters quantitatively; for example, tissue blood volume, blood flow, transit time and bolus arrival time. These measurements depend on the specific features of the contrast agent injection, including the type and amount of contrast agent, and the injection rate.

A residue function R(t), which measures the fraction of tracer remaining at a time t after the injection thereof may defined. The residue function may have the characteristics of a unit impulse response and decreases with time such that $R(0)=1$ and $R(\infty)=0$. A proportionality with the cerebral blood flow (CBF) exists, as the tracer concentration in a given tissue volume is proportional to the amount of blood passing through the tissue element per unit time.

$$C_t(t) = CBF \cdot C_\alpha \cdot R(t) \tag{1}$$

The product CBF·R(t) may be called the tissue impulse response function, as it is the concentration of tracer in the tissue arising from an impulse input. If the injection time were infinitively short, $C_\alpha$ would be a constant. However, in practice, a finite time is needed to inject tracer, and because the tracer becomes mixed with the blood in the vessel, and the resultant arterial tracer concentration is a function of time, perhaps like a bell-shaped curve, and this may be considered as the input function $C_\alpha(t)$. Accordingly, the tissue concentration time function becomes the convolution of the tissue impulse response function and the AIF, so that:

$$C_t(t) = CBF \cdot C_\alpha(t) \otimes R(t) \qquad (2)$$

where $\otimes$ is the convolution operator.

Thus, the tissue impulse response function R(t) may be determined by de-convolution. A quantification of hemodynamic parameters or a direct comparison between different examinations, either on different subjects or even on the same subject at different time, is thus feasible if the profile of the tracer injection, or the AIF, $C_\alpha(t)$ is known. Such comparisons are helpful for monitoring therapeutic interventions and following disease course. An absolute quantification of the hemodynamic parameters may also be useful in cases of diffuse diseases where a relative evaluation is not possible because an internal reference may be missing.

The AIF may be obtained by analysis of a sequence of images obtained by an imaging modality. As an example, consider an X-ray system capable of obtaining digital radiographs at a sufficiently rapid interval. Such an imaging modality may be a C-arm X-ray device, and shown as part of a treatment suite in FIG. 1. Other embodiments of the system may include more than, or fewer, than all of the devices, or functions, shown in FIG. 1.

The data processing and system control is shown as an example, and many other physical and logical arrangements of components such as computers, signal processors, memories, displays and user interfaces are equally possible to perform the same or similar functions. The particular arrangement shown is convenient for explaining the functionality of the system.

The C-arm X-ray device 20 may comprise a C-arm support 26 to which an X-ray source 22, and an X-ray detector 13 may be mounted so as to face each other about an axis of rotation. The C-arm 26 may be mounted to a robotic device 27 comprising a mounting device 7, and one or more arms 24 which are articulated so as to be capable of positioning the C-arm X-ray device with respect to a patient support apparatus 10. The robotic device 27 may be controlled by a control unit 26, which may send commands causing a motive device (not shown) to move the arms 24. The motive device may be a motor or a hydraulic mechanism. The mounting device may be mounted to a floor 40 as shown, to a ceiling or to a wall, and may be capable of moving in longitudinal and transverse directions with respect to the mounting surface.

The C-arm X-ray device 20 is rotatable in a plurality of planes such that projection X-ray images may be obtained by an X-ray detector 13 positioned on an opposite side of the patient from the X-ray source 22.

The projection X-rays images may be obtained as a sequence of images and the images may be reconstructed by any technique of processing for realizing 2D radiographic, or computed tomographic (CT)-like 3D images. A patient 50 may be positioned on a patient support apparatus 10. The patient support apparatus 10 may be a stretcher, gurney or the like and may be attached to a robot 60. The patient support apparatus 10 may also be attached to a fixed support or adapted to be removably attached to the robot. Aspects of the patient support apparatus 10 may be manipulable by the robot 60. Additional, different, or fewer components may be provided.

The devices and functions shown are representative, but not inclusive. The individual units, devices, or functions may communicate with each other over cables or in a wireless manner, and the use of dashed lines of different types for some of the connections in FIG. 1 is intended to suggest that alternative means of connectivity may be used.

The C-arm X-ray radiographic device 20 and the associated X-ray image processing 25 may produce 2D radiographic images or computed tomographic (CT) images comparable to, for example, closed-type CT equipment, while permitting more convenient access to the patient for ancillary equipment and treatment procedures. Alternatively CT or MR devices may be used as well.

A separate processor 35 may be provided for this image reconstruction and processing, or the function may be combined with other processing functions. The various devices may communicate with a DICOM (Digital Communications in Medicine) system 40 and with external devices over a network interface 44, so as to store and retrieve image and other patient data.

Images reconstructed from the X-ray data may be stored in a non-volatile (persistent) storage device 28 for further use. The X-ray device 20 and the image processing attendant thereto may be controlled by a separate controller 26 or the function may be consolidated with the user interface and display 11. The user interface and display 11 may be a computer workstation Alternatively, some of these functions may be performed on other computing devices, which may be remotely located and communicate with the radiographic suite over a network. The display of the images may be on a plurality of displays, of the display may have a plurality of display areas, which may independently display data. An operator may interact with the displays using graphical interaction tools, as is known.

The images may be obtained with or without various contrast agents that are appropriate to the imaging technology and diagnosis protocol being used.

For purposes of description, consider that 2D radiographic image data has been obtained by a beam of monoenergetic photons (e.g., X-rays) with an incident intensity $I_0$, penetrating a layer of material with thickness L and attenuation coefficient $\mu$ characteristic of the material layer. The incident radiation is partially absorbed by the material and the photon beam emerges from the exit side of the material with intensity I given by the exponential attenuation law $$I = I_0 e^{-\mu L}. \qquad (3)$$

In the patient being imaged, the attenuation coefficient of the tissue may vary along the ray path between the X-ray emitter and the detector. The resultant exit-beam intensity is decreased by the integral along the ray path of the incremental attenuation values of the material along the path, which may be tissue, bone, blood or the like.

A first image, which may be obtained prior to the administration of the contrast material may be termed a baseline image, mask image, or the like. During the course of administration of the tracer material, a sequence of images may be obtained, such that a plurality of images is obtained during the first transit time of the bolus of contrast material through the volume of interest. Such images may be termed "filled images" to suggest that the blood vessels are at least temporarily filled with a mixture of blood and tracer.

Let $I_f$ and $I_m$ denote the intensity of the filled and the mask images at a same pixel position, respectively. Then, $$I_m = I_0 e^{-(\mu_v l_v + \mu_b l_b)} \qquad (4)$$

and $$I_f = I_0 e^{-(\mu_c^{l_v} + \mu_b l_b)} \qquad (5)$$

where $l_v$ and $l_b$ are the total thickness of the filled vessels and background material along a ray path; and, $\mu_v$, $\mu_b$ and $\mu_c$ are the attenuation coefficients of the non-filled vessel, the background tissues, and the tracer, respectively.

The actual value of the incident intensity $I_0$ may be eliminated from the calculation by logarithmic subtraction of the data on a pixel-by-pixel basis:

$$\ln I_f - \ln I_m = \ln I_0 - \mu_c l_v - \mu_b l_b - \ln I_0 + \mu_v l_v + \mu_b l_b = -(\mu_c - \mu_v) l_v \approx -\mu_c l_v \quad (6)$$

The resultant difference is seen to be linearly proportional to the thickness of the tracer-filled vessel along the projection ray path. (Where 3-dimensional data is being analyzed, such as in data obtained by a CT or MRI device, the subtraction may be performed on a voxel-by-voxel basis. The functional transformation of the values of the elements of the voxel data sets being subtracted depends on the type of imaging modality and image processing being used).

The logarithmic subtraction of the mask image from each of the fill images provides a value that is proportional to the filled vessel thickness. Consequently, the sum of the logarithmic differences over all the pixels of the difference image may be used as a measure of the total tracer injected, provided that the wash-out from the imaged volume (tracer flows out of field of view through the main draining vein) has not started prior to completion of the tracer injection. As a result, the sum of the logarithmic difference between the baseline image and the subsequent images can be computed as:

$$F(t) = \sum_{x=0}^{N} (\ln I_f(x,t) - \ln I_m(x,t)) \quad (7)$$

$$\approx -\sum_{x=0}^{N} \mu_c(x,t) l_v(x,t)$$

$$= -\sum_{x=0}^{N} \frac{\mu_c(x,t)}{\rho(x,t)} \rho(x,t) l_v(x,t)$$

where t is the time of sampling and x the index of pixels.

$$\mu' = \frac{\mu_c(x,t)}{\rho(x,t)}$$

may be defined as the attenuation coefficient per unit mass of the contrast agent, and depends essentially on the photon energy, so the value of $\mu'$ may be considered as a constant as the energy does not change during an image acquisition sequence. A numeric value of $\mu'$ may be estimated either by simulation, by analytical computation or by empirical calibration. Since $\mu'$ is a constant, whose value may be determined, F(t) is a measure of the total tracer amount within the volume at time t.

For the images taken prior to the commencement of tracer outflow in the initial bolus pass, the rate at which contrast agent flows into the volume per unit time may be obtained by the first time derivative of the function F(t). This result is the AIF, $C_\alpha(t)$. The tissue response function of (2) may then be determined by a known de-convolution approach where (2) is solved for CBF·R(t). Standard mathematical de-convolution techniques, typically using a Fourier-transform technique or a linear algebraic approach are often used.

Other hemodynamic parameters may be determined from the tissue response function. For instance, the cerebral blood volume (CBV) may be calculated by integrating the area under the de-convolved tissue blood concentration curve, and the mean transit time (MTT) may be determined by the initial height of the CBV curve. The cerebral blood flow (CBF) may be determined by dividing the CBV by the MTT.

Thus the hemodynamic parameters may be determined without either explicitly measuring or controlling the time profile of the contrast agent injection or specifically analyzing the images to identify the time history of the contrast agent in the source artery. As such, this approach may be used in both prospective and retrospective analysis of clinical data even where manual injection of contrast agent has been performed, or where the information regarding the individual administrations of contrast agent are lacking in the medical records.

Where volumetric data is analyzed, such as for CT and MRI data, the resultant difference data for each voxel may be summed over all of the voxels in the volume to determine the concentration of tracer at any time. For the 2D angiographic images, only summation over the pixels is necessary, as the projection inherently contains the summation along the third axis.

The method, as described, is automatic, in that the analyst need not interact with the image acquisition and analysis. The results are more reproducible, as the overlap of multiple blood vessels along a ray path, or a ray path passing through a blood vessel at an oblique angle, does not affect the analytical result, by avoiding influence of vessel overlapping and non-right angularity which occurs inherently due to the ray path orientation as the measurement is an integral along the ray paths. In a procedure where a user selects a blood vessel for analysis, due to the specific projection used, the amplitude of the time-concentration curve is proportional to the total tracer amount along a projection ray, i.e. the overall thickness of the filled vessels along the ray path. This thickness varies with the amount of vessel overlapping and the spatial orientation of the vessel to the ray path, which is a function of the projection geometry. Such considerations are mitigated by the automatic method.

Figure 2:
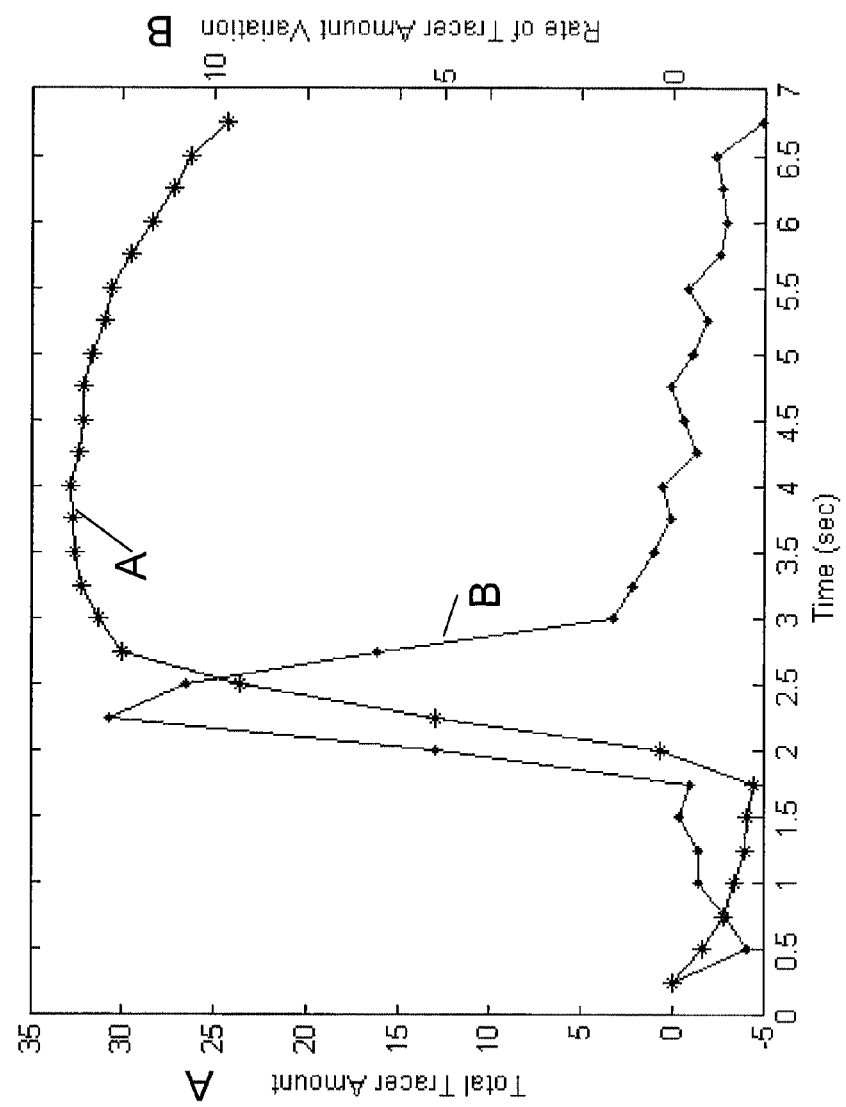
FIG. 2 is a graph showing the total tracer amount (curve A) as a function of time and the computed tracer concentration (curve B) computed as the temporal derivative of curve A, from a series of 2-D radiographic images.
Figure 3:
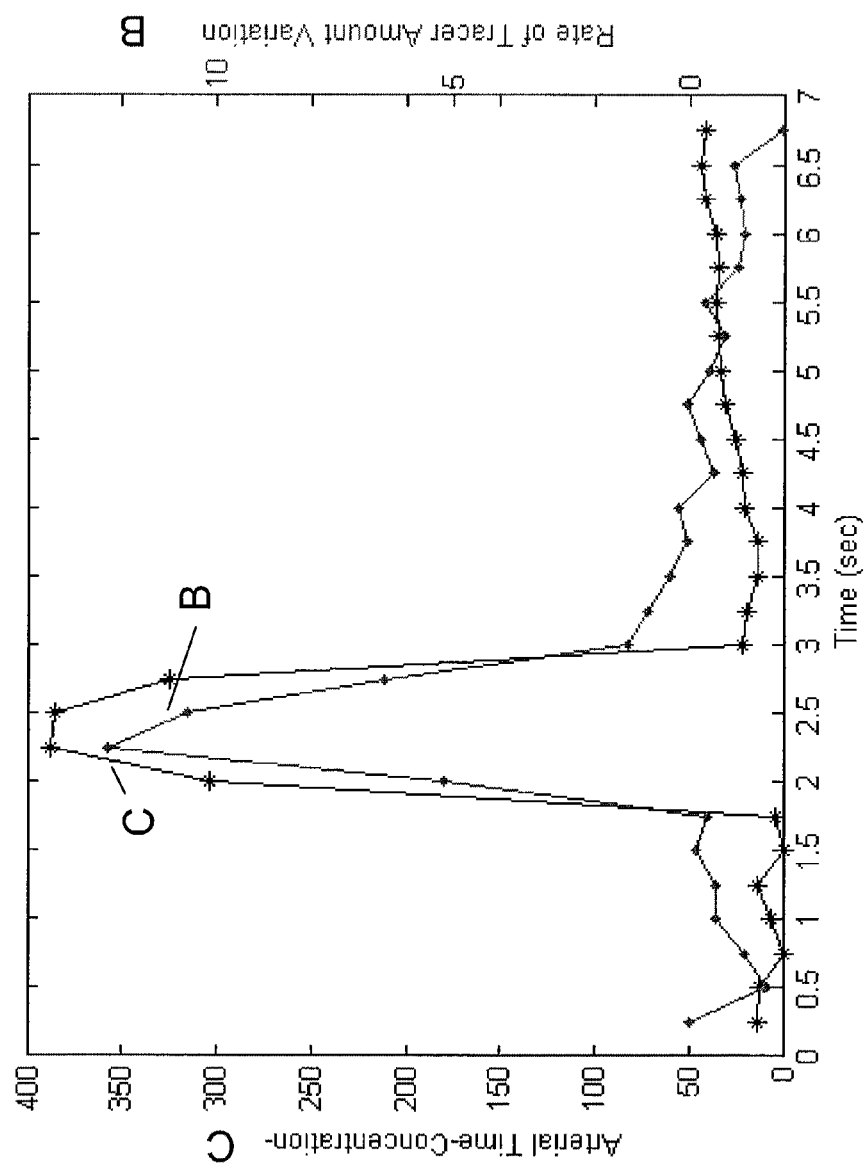
FIG. 3 is a graph comparing the computed tracer concentration (curve B) with a measured tracer concentration in a supply artery (curve C)

FIGS. 2-3 show an example of estimating the AIF. In FIG. 2, curve A represents the total tracer amount as a function of time as determined by (7), and curve B represents the temporal rate of tracer concentration variation, which is the time derivative of (7). For display purposes, the curves are shown with different scaling of the vertical axis. Both curves start to rise at 1.75 sec. Curve A builds to a plateau after approximately 3 seconds, and the plateau lasts about 2 seconds, after which the curve slowly declines. The flowing of tracer from the artery to parenchyma, and then to the vein, is not an infinitively short progress. Rather, the contrast agent bolus begins to arrive in the parenchyma at the time when the contrast agent begins to flow out of the artery. That is, the time of bolus arrival in the parenchyma is approximately equal to the time of peak concentration in the artery. Similarly, the time of first arrival of the contrast agent in the outlet vein is approximately equal to the time of peak concentration of the contrast agent in the parenchyma. Consequently, after the contrast agent flows completely out of the feeding artery, perhaps at 3.5 seconds, the effects of outflow from the parenchyma to the vein begin to be observed. During the plateau period, the contrast agent may redistributed in the volume; however, there is not a significant inflow to, or outflow from, the volume at that time.

In FIG. 3 curve C represents a sampled time-concentration curve at a region within the supplying artery. Curve B is the same curve as the curve B in FIG. 2. Curve C was obtained from the same image data set as Curve B, however the analysis was performed manually. A location in the artery was selected, and the time variation of the concentration of the contrast agent was measured by selecting the appropriate pixels and determining the difference between the logarithm of the intensity of the image in the selected location and that of the image taken prior to the administration of the contrast agent. This required the manual identification of an appropriate pixel or group of pixels in the image. That is, the same data set was analysed using the methods described herein and by a manual method.

Figure 4:
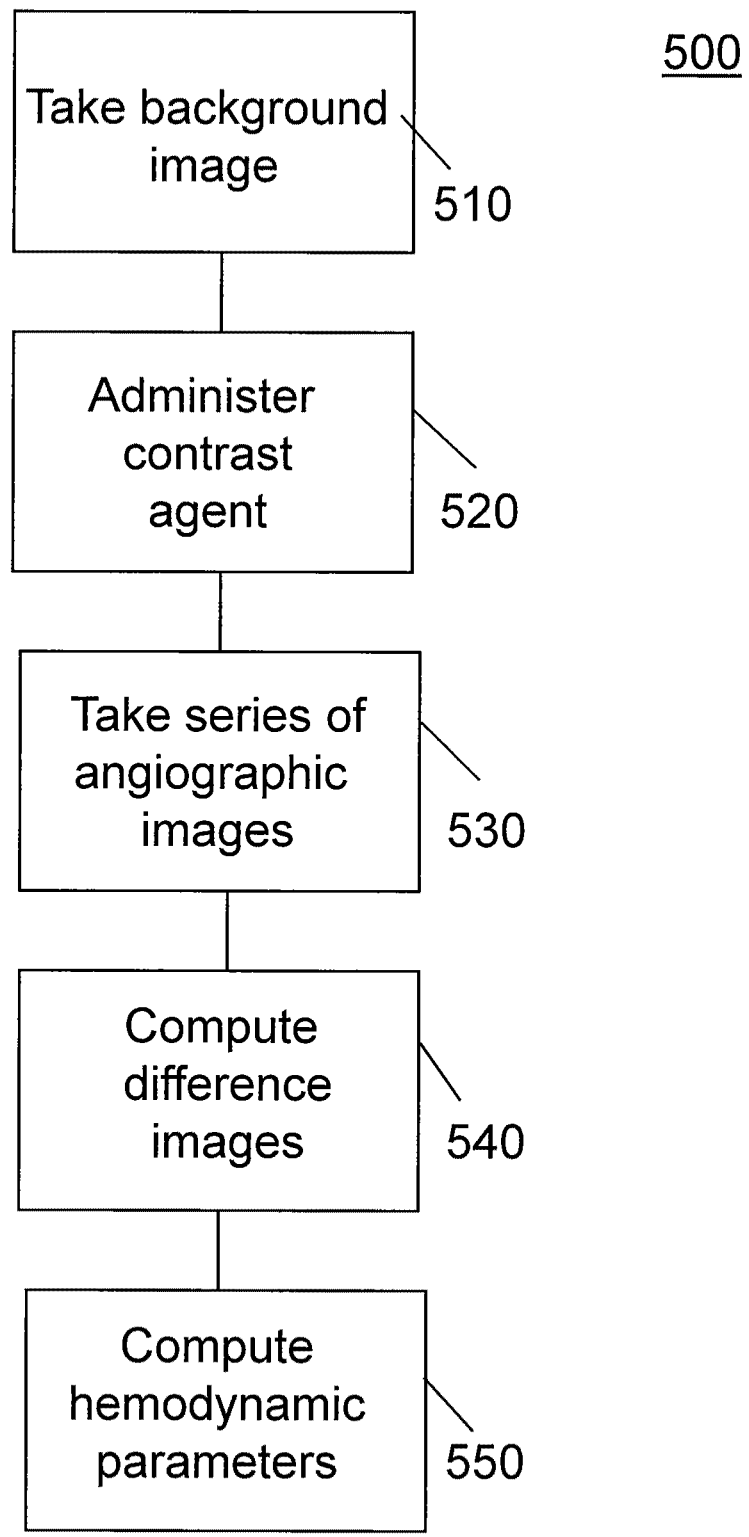
FIG. 4 is a flow chart of a method of determining the arterial input function.
Figure 5:
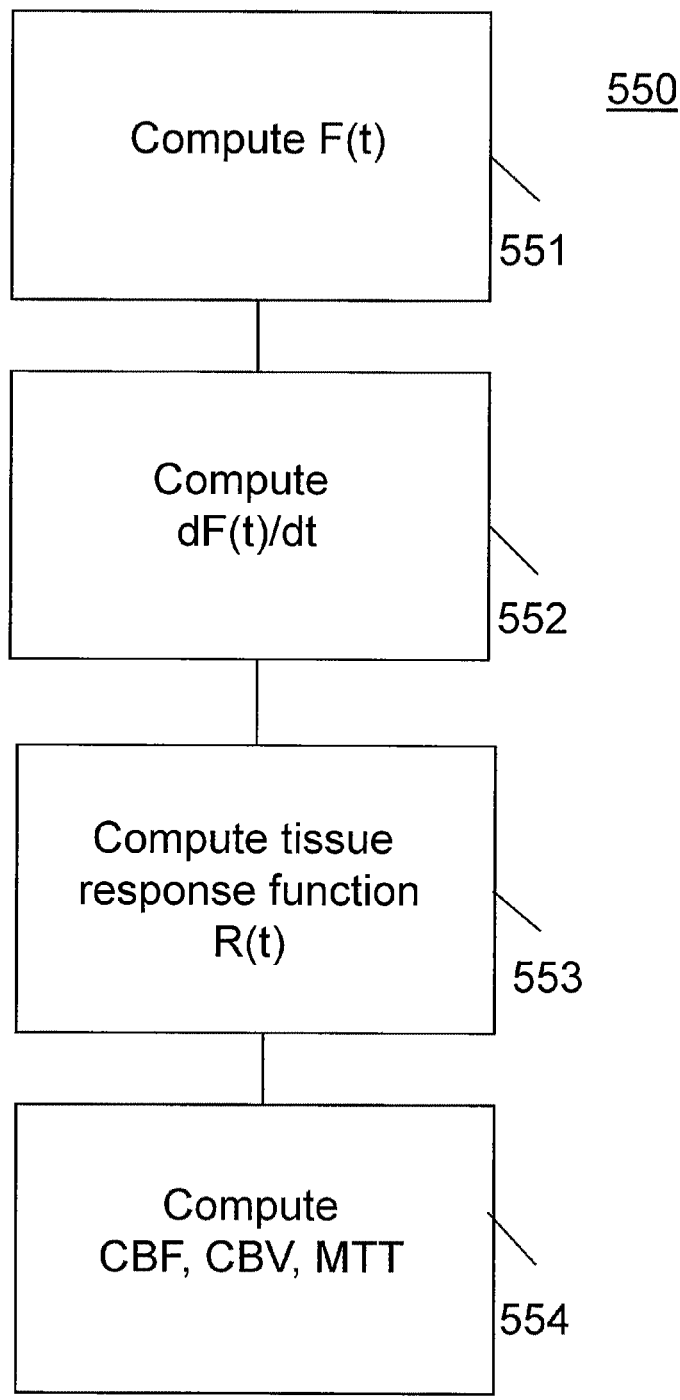
FIG. 5 is a deal of the method of FIG. 4.

A clinical workflow to support the performance of a procedure to determine the hemodynamic parameters is shown in FIG. 4.

In an example, a method 500 of determining hemodynamic parameters for a patient brain includes the steps of preparing the patient for a radiological examination, and taking a background image of the brain (step 510). A contrast agent is subsequently administered (step 520) and a series of angiographic images is taken in rapid succession (step 530). The temporal spacing of the images is a trade-off between the granularity of measurement of a time-varying situation and the total radiation dose administered to the patient, and is a matter of medical judgment. An example of the granularity may be seen by the spacing of data points in FIGS. 2-3.

The data obtained during the first passage of the contrast agent bolus through the brain is logarithmically subtracted from the background image (step 540) for 2D radiographs, and the difference images are used to compute the hemodynamic parameters.

In more detail, step 550 may include computing the amount F(t) from the subtraction image (step 551) and determining the arterial input function AIF by differentiating the amount curve (step 552). The AIF and the concentration curve may be de-convolved so as to yield the tissue response function R(t) (step 553) and the desired hemodynamic parameters computed as previously described (step 554).

While the methods disclosed herein have been described and shown with reference to particular steps performed in a particular order, it will be understood that these steps may be combined, sub-divided, or reordered to from an equivalent method without departing from the teachings of the present invention. Accordingly, unless explicitly stated, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A system for determining hemodynamic parameters of a patient, the system comprising:
 a medical imaging device; and
 a computer adapted to:
  receive a first image data set from the medical imaging device;
  receive a plurality of temporally resolved second image data sets from the medical imaging device, the second image data sets being obtained after administration of a contrast agent;
  subtract a value of each element of the first image data set from a value of each element of a series of second image data sets of the plurality of temporally resolved second image data sets to form a plurality of third image data sets;
  sum pixel or voxel data of an image data set of the plurality of third image data sets over a volume to determine an amount of contrast agent for each third image data set of the plurality of third image data sets; and
  calculate a time derivative of a time series of the amount of contrast agent.

2. The system of claim 1, wherein the medical imaging device is a C-arm X-ray device.

3. The system of claim 1, wherein each element of the first image data set and the second image data sets is a pixel of a 2-D radiographic image, and
 wherein the computer is adapted to calculate logarithmic differences by subtracting a logarithm of a value of each pixel of the first data set from a logarithm of a value of each corresponding pixel of the series of second image data sets.

4. The system of claim 1, wherein the medical imaging device is a computed tomographic X-ray device.

5. The system of claim 1, wherein the medical imaging device is a magnetic resonance imaging device.

6. The system of claim 1, wherein the medical imaging device and the computer are connected over a network.

7. The system of claim 1, wherein the differentiated time series of the amount of contrast agent is an estimate of an arterial input function.

8. The system of claim 1, wherein the computer is adapted to deconvolve an arterial input function from a time-concentration course of each pixel or voxel, such that a tissue impulse response is determined.

9. The system of claim 1, wherein the computer is adapted to compute hemodynamic parameters using the plurality of third image data sets, the hemodynamic parameters including a cerebral blood volume (CBV), a cerebral blood flow (CBF), a mean transit time (MTT), or a combination thereof.

10. A method of determining hemodynamic parameters, the method comprising:
 receiving a first image data set of a patient;
 receiving a plurality of second image data sets of the patient, the second image data sets being obtained during a first passage of a contrast agent bolus through a parenchyma;
 computing a plurality of third image data sets by subtracting a value of each element of the first image data set from a value of a corresponding element in the second image data sets;
 computing an amount of contrast agent in the parenchyma for image data sets of the plurality of third image data sets; and
 computing a time derivative of the amount of contrast agent to determine an arterial input function.

11. The method of claim 10, further comprising computing hemodynamic parameters, the hemodynamic parameters including a cerebral blood flow (CBF), a cerebral blood volume (CBV), a mean transit time (MTT), or a combination thereof.

12. The method of claim 10, wherein the elements of the first image data set and the elements of the second image data sets are pixels.

13. The method of claim 11, wherein the first image data set and the second image data sets are obtained by a C-arm X-ray device.

14. The method of claim 12, wherein a logarithm of intensity values of the pixels of the first image data set are subtracted from a logarithm of intensity values of corresponding pixels of the second image data sets.

15. The method of claim 10, wherein the elements of the first image data set and the elements of the second image data sets are voxels.

16. The method of claim 15, wherein the first image data set and the second image data sets are obtained by a computed tomographic (CT) device or a magnetic resonance imaging (MR) device.

17. The method of claim 10, wherein the parenchyma is a brain.

18. A computer program product stored or distributed on a computer readable memory, the computer readable memory comprising instructions configuring a computer to:
receive a first image data set of a patient;
receive a plurality of second image data sets of the patient, the second image data sets being obtained during a first passage of a contrast agent bolus through a parenchyma;
compute a plurality of third image data sets by subtracting a value of each element of the first image data set from a value of a corresponding element of the second image data sets;
compute an amount of contrast agent in the parenchyma for image data sets of the plurality of third image data sets; and
compute a time derivative of the amount of contrast agent to determine an arterial input function.

19. The computer program product of claim 18, wherein the values of the elements of first image data set and the second image data sets are the logarithm of measured intensities, when two dimensional radiographic images are used.

20. The system of claim 3, wherein the computer is adapted to calculate a value representing a total amount of contrast administered by summing the logarithmic differences.

* * * * *